United States Patent [19]
Buysch et al.

[11] Patent Number: 5,728,897
[45] Date of Patent: Mar. 17, 1998

[54] PROCESS FOR THE PREPARATION OF BENZYL ALCOHOL

[75] Inventors: Hans-Josef Buysch, Krefeld; Erhard-Günther Hoffmann, Ratingen; Ursula Jansen; Pieter Ooms, both of Krefeld; Bernd-Ulrich Schenke, Bottrop, all of Germany

[73] Assignee: Bayer Aktiengesellschaft, Leverkusen, Germany

[21] Appl. No.: 655,719

[22] Filed: May 30, 1996

[30] Foreign Application Priority Data

Jun. 6, 1995 [DE] Germany .............. 195 20 612.6

[51] Int. Cl.$^6$ ..................................................... C07C 33/34
[52] U.S. Cl. ..................................................... 568/715
[58] Field of Search .............................................. 568/715

[56] References Cited

U.S. PATENT DOCUMENTS 2,221,882  11/1940  Rosenberg .
4,474,993  10/1984  Hag et al. .

FOREIGN PATENT DOCUMENTS 484662   of 1926  Germany .
2101810  7/1972   Germany .
161067   9/1984   Germany .

OTHER PUBLICATIONS

Kirk–Othmer; Encyclopedia of Chemical Technology;Third Edition;vol.5; pp. 828–830, 1979.
Ann. 196,353, 1879.
M. Simonetta, et al, J. Chem. Soc., pp. 1840–1844 (1954).
H. Bohme, et al., Z. Naturforschg., pp. 580–584 (1946).
B. Bensley, et al., J. Chem. Soc., pp. 4747–4754 (1957).
P.J.C. Fierens, et al., vol. 1, pp. 129–144 (1957); (Tetrahedron).
S.C.J. Olivier, Rec., vol. 48, pp. 227–236 (1929).
S.C.J. Olivier, Rec., vol. 49, pp. 667–704, (1930).
G.W. Beste, et al., J. Am. Chem. Soc., vol. 62, pp. 2481–2487, (1940).
S.C.J. Olivier, Rec., vol. 53, pp. 891–894 (1934).
S.C.J. Olivier, et al., Rec., vol. 53, pp. 869–890, (1934).
H. Limpricht, Ann., 139, 303–327 (1866).
G. Niederist, Ann., vol. 196, pp. 349–360, (1879).
F. Bruhne in "Ullmann's Encyclopeida of Chemistry", 5th ed., vol. 4, pp. 1–8, Verlag Chemie, Weinheim (1988).
H. Henzler in "Ullmanns's Encyclopedia of Industrial Chemistry," 5th ed., vol. B4, pp. 561–586, Verlag Chemie, Weinheim (1992).

*Primary Examiner*—Gary Geist
*Assistant Examiner*—Sreeni Padmanabhan
*Attorney, Agent, or Firm*—Sprung Kramer & Schaefer & Briscoe

[57] ABSTRACT

A novel process for the preparation of benzyl alcohol by the hydrolysis of benzyl chloride, which operates with from 10 to 70 times the molar quantity of water at temperatures of from 80° to 180° C. and stops the reaction before complete conversion is reached, avoids both the addition of bases and water-soluble organic solvents and also the formation of sodium chloride.

1 Claim, No Drawings

PROCESS FOR THE PREPARATION OF BENZYL ALCOHOL

The present invention relates to a process for the preparation of benzyl alcohol by the hydrolysis of benzyl chloride with water in a molar ratio of 1:10 to 1:70 at 80° to 180° C., in which the reactants are intensively mixed together without addition of a water-soluble auxiliary, the reaction is stopped when conversion is incomplete and the reaction mixture is worked up.

Very much has already been reported concerning the hydrolysis of benzyl chloride. Several publications concern themselves with this problem with a view to elucidating the reaction mechanism and developing analytical methods. In this connection, homogeneous mixtures of benzyl chloride, water and a water-soluble solubilizer such as alcohol, acetone, dioxan or acetic acid are usually used; see, for example, J. Chem. Soc. 1954, 1840 ff; Z. Naturf. 1946 (1) 580–4, J. Chem. Soc. 1957, 4747 ff; Tetrahedron 1957 (1) 129–144; Rec. 48, 227 ff (1929) and 49, 667 ff (1930). In various cases the hydrolysis is also performed in the presence of alkali metal hydroxides, alkali metal carbonates or alkaline earth metal carbonates, as, for example, in J. Am. Chem. Soc. 62, 2481 (1940), Rec. 53, 891 ff and 869 ff (1934), where the last-mentioned publications show that the hydrolysis is accelerated in the presence of basic compounds. In all these papers, no value is given to the isolation and identification of the hydrolysis products.

However, there are also investigations into the hydrolysis of benzyl chloride with water only, which include a description of the hydrolysis products. According to Ann. 139, 307 f (1866), benzyl chloride at 190° C. is converted by water mainly into hydrocarbons and dibenzyl ether.

Under milder conditions [(Ann. 196., 353 (1879)] at temperatures from 100° to 110° C. and with complete conversion a yield of benzyl alcohol—although in very great dilution—of 76% of theory is obtained; the remaining materials were high boiling substances that were not characterized.

The realization that the conversion in the presence of alkalis proceeds more rapidly and more smoothly led, in the industrial sector, to an early attempt to bind the hydrochloric acid formed during the hydrolysis of benzyl chloride. Thus, in DRP 484 662 it is recommended that the reaction should be performed in the presence of calcium carbonate, and in U.S. Pat No. 2 221 882 the reaction is performed first in the presence of a solution of sodium carbonate and subsequently a solution of sodium hydroxide. The yield is considerably greater than 90% of theory.

Sodium carbonate as a base has often been found to be useful, and was retained during later times. The further developments in this field were concerned with the industrial use of this basic hydrolysis of benzyl chloride as a continuous process, as described in DE-OS (German Published Specification) 2 101 810, EP-A 64 486 and DD Patent Specification 161 067.

However, disadvantages of the alkaline hydrolysis are the additional use of sodium carbonate, the formation of sodium chloride and the production of large amounts of aqueous waste liquors which have to be disposed of.

The object of the present invention is to develop a novel process that avoids the addition of sodium carbonate and hence the sodium chloride and waste water problems.

It has now been found that this object is in practice achieved with at least equal or better yields of benzyl alcohol if benzyl chloride is allowed to react with water in a molar ratio from 1:10 to 1:70 at temperatures between 80° C. and 180° C. with intensive mixing under incomplete conversion.

According to the state of knowledge, the result was in no way to be expected: the yields which had hitherto become known were moderate, and the nature of the by-products was not known. The 76% yield of benzyl alcohol obtained under mild conditions at temperatures from 100° C. to 110° C. [Ann. 196, 353 (1879)] was obtained with a molar ratio water: benzyl alcohol of 190:1, i.e. a weight ratio of 27:1; this means that the hydrochloric acid obtained on the one hand in fact had a very low concentration and therefore could hardly be implicated in by-product formation, but on the other hand was of no value as a useful material.

Furthermore, under these conditions, an industrially unacceptably low space-time yield was to be expected.

On the other hand, a reduction of the molar ratio from 190:1 to the values, in accordance with the claims, of from 10:1 to 70:1 would necessarily involve a considerably increased formation of by-products, because the hydrochloric acid concentration and hence its activity increases by a large factor.

In contrast, the process of the invention gives a hydrochloric acid of higher concentration as a coproduct which can be reused.

A suitable starting material for the process of the invention is benzyl chloride as is usually available by side chain chlorination.

Benzyl chloride substituted by halogen such as chlorine, carboxyl, cyano, methoxy, methyl and nitro is of course also suitable. However, unsubstituted benzyl chloride is preferable.

The temperature range in which the reaction is carried out is from 80 to 180, preferably from 85 to 170, particularly preferably from 90° to 160° C.

The molar ratio of water to benzyl chloride is preferably from 55:1 to 15:1, particularly preferably from 50:1 to 20:1.

The conversion of benzyl chloride is from 35 to 99%, preferably from 40 to 90%, particularly preferably from 45 to 85%.

When the reaction is performed at temperatures above 100° C., this must be carried out at increased pressure because of the vapour pressure. The required overpressure is then at least equal to the vapour pressure of the reaction mixture. It can be up to about 50 bar, preferably up to 25 bar.

The intensive mixing together of the reaction partners can be carried out by various methods known to the person skilled in the art, for example by stirring, jets, baffles, static mixers, pumps, turbulent flow in narrow tubes and by ultrasound.

Devices of this type are described in more detail in Ullmann's Encyclopedia of Industrial Chemistry, 5th edn., Series B, Unit Operations, Sections 25, 26 B4, pp. 568–570, Verlag Chemie, Weinheim 1988.

The required reaction times in the process of the invention are unexpectedly short. The abovementioned conversions of benzyl chloride from 35 to 99% are reached in a few minutes to some hours, for example in 2 to 240, preferably 3 to 180, particularly preferably 4 to 120 min.

According to the process of the invention, a yield of benzyl chloride from >90 to about 96% is obtained, which is thus greater than the 85% obtainable by alkaline hydrolysis, Ullmann's Encyclopedia of Industrial Chemistry, 5th edn., Vol. 4, p. 3, Weinheim. The by-product is dibenzyl ether, as in current industrial processes.

The process of the invention thus corresponds to a synthesis of benzyl alcohol without sodium carbonate and without wastewater, since the hydrochloric acid obtained can be concentrated by absorption of HCl from the chlorination and industrially reused, or can be converted back into chlorine by hydrochloric acid electrolysis.

Benzyl alcohol is suitable for use as a plasticizer and solvent in the paint industry, as a solvent for odoriferous materials and for specific applications in the processing of rubber and textiles.

In the following examples, the percentage figures are percentages by weight.

EXAMPLES

EXAMPLE 1

126.5 g (1 mol) of benzyl chloride and 180 g (10 mol) of water were rapidly heated to reflux in a flask with baffles and propeller stirrer with vigorous stirring (250 rpm) under nitrogen. After 240 min reaction time, the mixture was rapidly cooled, the organic phase was separated off after addition of toluene, and analyzed by gas chromatography. It was found that 48 g of the benzyl chloride had been converted to give a yield of benzyl alcohol of 37 g and about 3.6 g dibenzyl ether, corresponding to a conversion of 38% and a yield of benzyl alcohol of 91%. The hydrochloric acid formed had a concentration of about 7.4%.

EXAMPLE 2

126.5 g (1 mol) of benzyl chloride and 720 g (40 mol) of water were stirred in a flask as described in Example 1 for 2 h and then rapidly cooled. After isolation and analysis of the organic phase, as in Example 1, it was found that the conversion of benzyl chloride was 76% and the yield of benzyl alcohol based on this conversion was 94%. Dibenzyl ether was again a by-product. The hydrochloric acid formed contained about 3.8% HCl.

EXAMPLE 3

Example 2 was repeated, but with 360 g (20 mol) of water and was stopped after 180 min. The conversion at that point was 64%, and the yield of benzyl alcohol 91%.

EXAMPLE 4

Example 2 was repeated, but with 900 g (50 mol) of water, and was stopped after 120 minutes. The conversion at that point was 92% and the yield of benzyl alcohol 94%.

EXAMPLE 5

Example 4 was repeated, but until the conversion was 97%, corresponding to a running time of 3 h. The yield of benzyl alcohol was 91%.

EXAMPLE 6

Example 2 was repeated, but with 70 mol of water and 2 h running time. This gave a conversion of 99% and a yield of benzyl alcohol of 94%.

EXAMPLE 7

Example 2 was repeated, but at 85° C. and a running time of 4.5 h. A conversion of 52% and a yield of benzyl alcohol of 96% was obtained.

EXAMPLE 8

Example 2 was repeated in an autoclave at 110° C. After 50 min running time, a conversion of 65% and a yield of benzyl alcohol of 95% was obtained.

EXAMPLE 9

Example 2 was repeated in an autoclave at 120° C. After 15 min running time, a conversion of 60% and a yield of benzyl alcohol of 96% was obtained.

EXAMPLE 10

Example 2 was repeated in an autoclave at 130° C. After 10 min, a conversion of 85% and a benzyl alcohol yield of 93% was obtained.

EXAMPLE 11

Example 2 was repeated in an autoclave at 140° C. After 7 min running time, a conversion of 85% and a yield of benzyl alcohol of 91% was obtained.

EXAMPLE 12

Example 2 was repeated in an autoclave at 150° C., but with 540 g (30 mol) water. After 4 min running time, a conversion of 64% and a yield of benzyl alcohol of 94% was obtained.

We claim:

1. Process for the preparation of benzyl alcohol by the hydrolysis of benzyl chloride with water at elevated temperature, characterized in that the hydrolysis is performed at a molar ratio of benzyl chloride to water of from 1:10 to 1:70, at temperatures of from 80° to 180° C. and for a reaction time of 2 to 240 minutes until the conversion of benzyl chloride is from 35 to 99% and the yield is over 90% without addition of a base and without addition of a water-soluble organic solvent.

* * * * *